(12) United States Patent
Chiari et al.

(10) Patent No.: US 7,867,140 B2
(45) Date of Patent: Jan. 11, 2011

(54) DEVICE FOR CONDITIONING BALANCE AND MOTOR CO-ORDINATION

(75) Inventors: Lorenzo Chiari, Bologna (IT); Fay B. Horak, Portland, OR (US); Angelo Cappello, Bologna (IT); Dozza Marco, Bologna (IT)

(73) Assignees: Alma Mater Studiorum-Universita Di Bologna, Bologna (IT); Oregon Health and Sciences University, Portland, OR (US)

( * ) Notice: Subject to any disclaimer, the term of this patent is extended or adjusted under 35 U.S.C. 154(b) by 56 days.

(21) Appl. No.: 11/570,290

(22) PCT Filed: Jun. 14, 2004

(86) PCT No.: PCT/IB2004/001679
§ 371 (c)(1),
(2), (4) Date: May 9, 2007

(87) PCT Pub. No.: WO2006/005978
PCT Pub. Date: Jan. 19, 2006

(65) Prior Publication Data
US 2007/0249466 A1 Oct. 25, 2007

(51) Int. Cl.
*A63B 15/02* (2006.01)
*A63B 71/00* (2006.01)

(52) U.S. Cl. ............................ 482/1; 600/595; 73/865.4

(58) Field of Classification Search ................. 482/1–9; 600/49, 595; 607/48–49, 62
See application file for complete search history.

(56) References Cited

U.S. PATENT DOCUMENTS

| | | | |
|---|---|---|---|
| 5,221,088 A * | 6/1993 | McTeigue et al. | 473/201 |
| 5,304,984 A | 4/1994 | Roldan | |
| 5,372,365 A * | 12/1994 | McTeigue et al. | 473/409 |
| 5,694,340 A * | 12/1997 | Kim | 702/141 |
| 5,728,027 A | 3/1998 | Sinaiko | |
| 5,790,958 A * | 8/1998 | McCoy et al. | 455/557 |
| 5,919,149 A * | 7/1999 | Allum | 600/595 |
| 6,063,046 A | 5/2000 | Allum | |
| 6,546,291 B2 * | 4/2003 | Merfeld et al. | 607/62 |
| 2004/0094613 A1 * | 5/2004 | Shiratori et al. | 235/105 |

* cited by examiner

*Primary Examiner*—Loan Thanh
*Assistant Examiner*—Shila Abyaneh
(74) *Attorney, Agent, or Firm*—Occhiuti Rohlicek & Tsao LLP

(57) ABSTRACT

A device for conditioning the balance and motor co-ordination of a user (2) comprises a system (3) for acquisition of information relative to the kinematics of at least one part (4) of the body of the user (2), a processing interface (9) connected to the acquisition system (3) to encode the information in a signal, a pair of earphones (12, 13) operating between the processing interface (9) and the user (2), to feed the user the signal suitably defined by a stereophonic sound which can be transmitted in an audio channel.

10 Claims, 3 Drawing Sheets

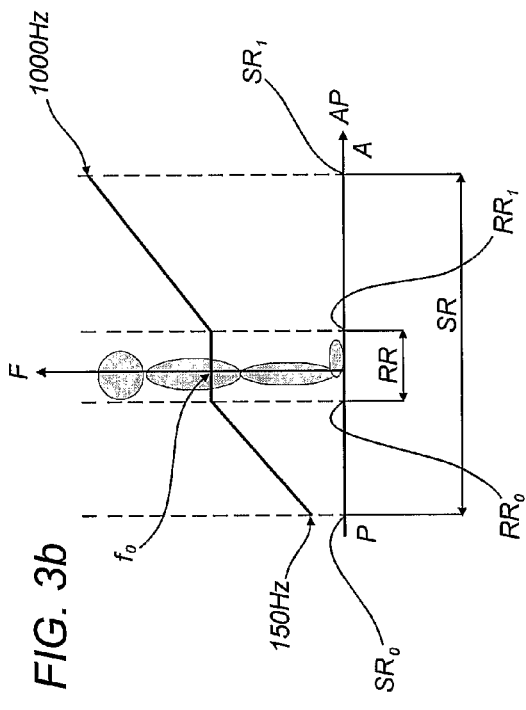
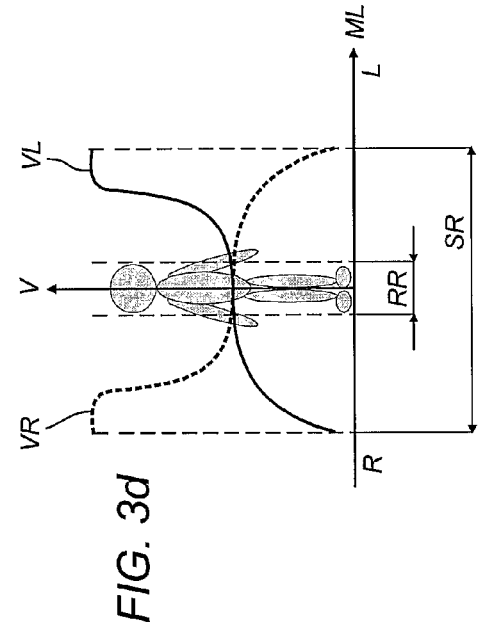
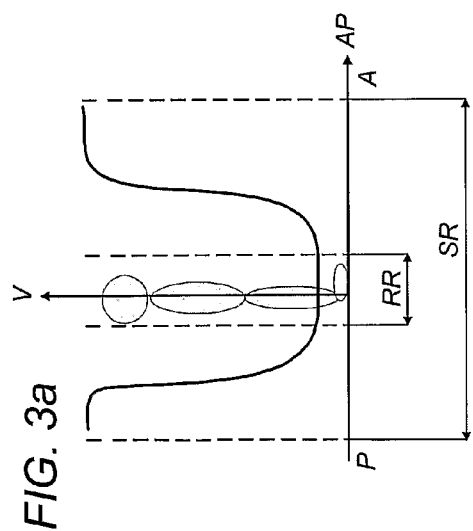
FIG. 3a  FIG. 3b  FIG. 3c  FIG. 3d

DEVICE FOR CONDITIONING BALANCE AND MOTOR CO-ORDINATION

CROSS-REFERENCE TO RELATED APPLICATIONS

This application is a national phase application under 35 U.S.C. 371 of PCT International Application No. PCT/IB2004/001679, filed Jun. 14, 2004.

TECHNICAL FIELD

The present invention relates to a device for conditioning balance and motor co-ordination.

In particular, it relates to a device which can be worn by a user, for quantifying, improving and training posture, balance and motor co-ordination in humans.

BACKGROUND ART

The erect position typical of mankind is intrinsically unstable due to the action of gravity and maintaining it, that is to say, the ability to keep one's balance, is a basic requirement for body movement.

Closely linked to this are the abilities to carefully control one's posture and to effectively co-ordinate the movements of the different parts of the body.

Therefore, the control of balance, posture and co-ordination have a role of central importance in the wider context of motor control and substantially depend on the subject's perception of the spatial positioning of his/her body or part of it.

It is known that ageing and any neural, muscular or skeletal disorder which compromises the senses may, in practice, result in a diminished motor ability and, in particular, a higher risk of postural instability and falls.

For this reason, the invention of systems for training, maintaining, rehabilitating or monitoring motor ability which have positive effects on balance, posture and motor co-ordination is currently strategic in a society in which the average age is gradually increasing.

Devices have been invented which help maintain balance, for people with motor difficulties and, in particular, devices able to provide the user with information about the spatial orientation of at least one part of his/her body.

Consider, for example, the device described in U.S. Pat. No. 6,546,291, which generally comprises an acquisition system, preferably wearable by the user, for detecting the spatial orientation and movement of the user or part of his/her body.

The acquisition system communicates, by means of a communication interface and an encoder, with a stimulator apparatus connected to the user's nervous system.

The stimulator apparatus comprises at least one electrode, located close to one of the user's nerves, by means of which a signal, suitably generated by the encoder according to the spatial orientation detected, stimulates said nerve, providing the user with an indication of his/her spatial orientation.

The device has several disadvantages, in particular direct stimulation of the nerve is not always easy to achieve and correct positioning of the electrode for this purpose may be awkward and ineffective, particularly in the case of elderly users.

The device also being dedicated to people with motor difficulties, these people may find it difficult to position and secure the stimulating electrodes on the body and guarantee that they remain in the correct position.

DISCLOSURE OF THE INVENTION

The aim of the present invention is to produce an improved device for conditioning balance and motor action which, by means of a control signal, provides the user with an indication of his/her position without acting directly on the user's nerves, that is to say, a substantially non-invasive device for conditioning balance and motor action.

Another aim of the present invention is to produce a device which is easy to use and easy to wear even for persons with motor deficiencies.

BRIEF DESCRIPTION OF THE DRAWINGS

The technical features of the present invention, in accordance with the above-mentioned aims, are set out in the claims herein and the advantages more clearly illustrated in the detailed description which follows, with reference to the accompanying drawings, which illustrate a preferred embodiment of the invention without limiting the scope of the inventive concept, and in which:

FIGS. 3a to 3d are schematic illustrations of a preferred trend of the parameters forming the control signal in the device illustrated in FIG. 1.

DETAILED DESCRIPTION OF THE PREFERRED EMBODIMENTS OF THE INVENTION

Figure 1:
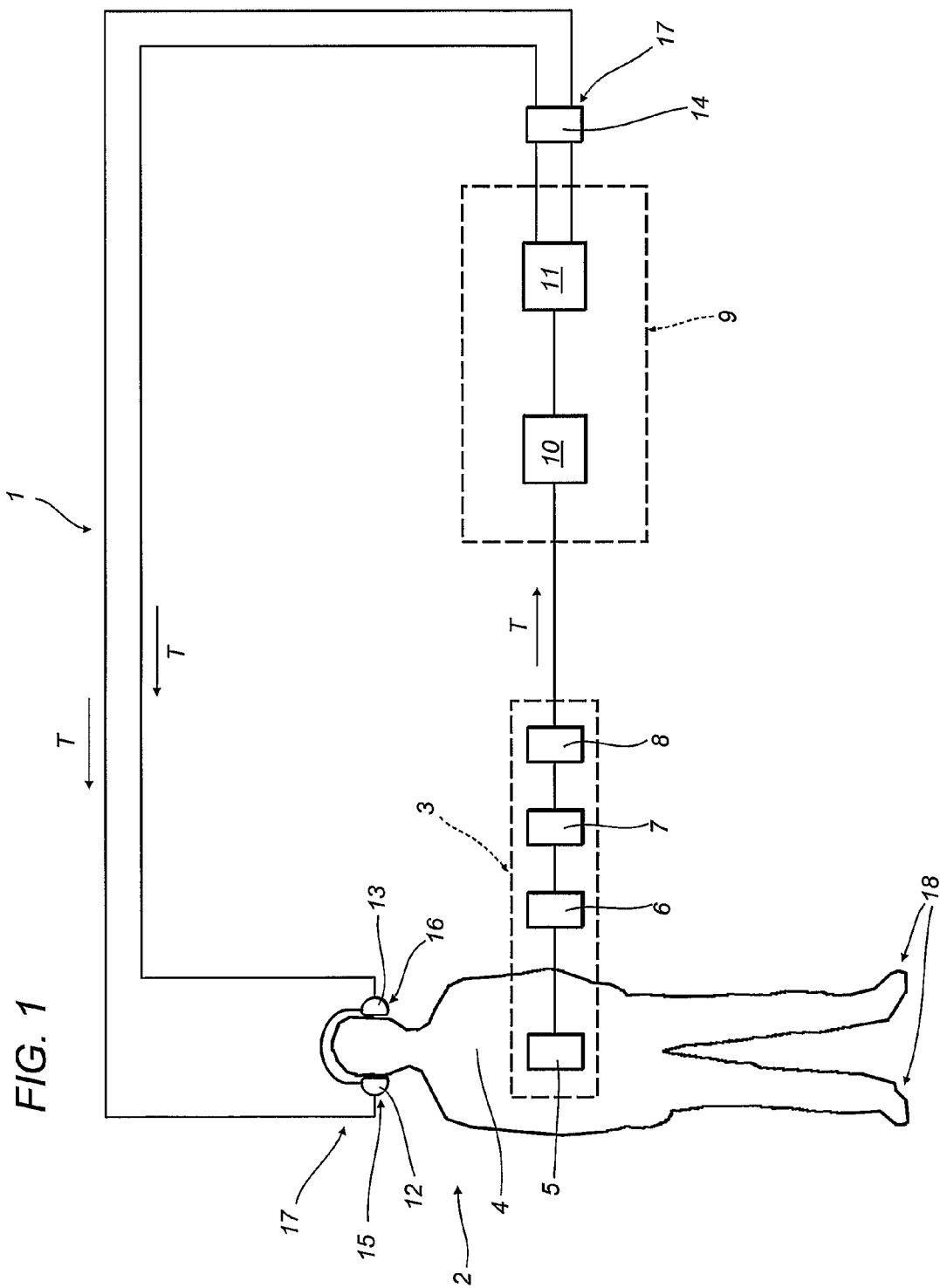
FIG. 1 is a schematic view of a device for conditioning balance and motor action in accordance with the present invention.

With reference to the accompanying drawings, the numeral 1 denotes a device for conditioning the balance of a user 2.

The device 1, which can be completely worn by the user 2, comprises a system 3 for the acquisition of information relative to the kinematics of a part 4 of the body of the user 2.

In more detail, the system 3 preferably has an accelerometric sensor 5 or accelerometer of the substantially known type (for example, biaxial or triaxial), connected to the torso of the user 2 and fitted with a preamplifier 6.

With a set direction T of feed of the data flow, the system 3 comprises, downstream of the accelerometer 5 preamplifier 6, an amplifier 7 and a filter 8 for conditioning an electrical signal generated by the accelerometer 5.

The accelerometer 5 translates the accelerations of the torso of the user 2 into electrical signals which, suitably conditioned, become intelligible to a processing system 9 connected to the acquisition system 3 and located downstream of the latter according to the direction T.

In alternative embodiments, not illustrated, the acquisition system 3 comprises a number of accelerometric sensors 5 and relative preamplifiers 6, amplifiers 7 and filters 8, greater than one according, for example, to the accuracy of the measurements to be taken or the anthropometry of the user 2.

The preamplifiers 6, amplifiers 7 and filters 8 are substantially of the known type and therefore not described in detail.

Is should be observed that the sensors 5 may be attached to any part 4 of the body of the user 2 depending on the area of the body to be improved, trained or subjected to posture analysis.

The processing system 9 comprises an analogue-digital converter 10 which receives at input the signal generated by the accelerometer 5.

Downstream of the converter 10, relative to the direction T, the system 9 comprises an electronic card 11 of the substantially known type, which, as described in more detail below, calculates the volume, frequency and balance of a control or feedback signal, derived from the electrical signal generated by the devices upstream.

In greater detail, using a suitable software not described in detail, the card 11 generates a stereophonic sound consisting of two sound waves.

The sound waves have their frequency and volume modulated and the stereophonic sound is suitably balanced between two audio channels, right and left, linked to respective earphones 12 and 13, right and left respectively, by way of example with reference to FIG. 1, which can be worn by the user 2. The right and left channels can be modulated independently of one another.

Advantageously, in the preferred embodiment, these sound waves are of the sinusoidal type, yet can assume any trend suitable for transmission of the information, as described below.

Downstream of the card 11 according to the direction T, the device 1 comprises an audio amplifier 14, of the known type, through which the stereophonic sound reaches the earphones 12 and 13.

The earphones 12 and 13 respectively consist of sound transducers 15 and 16 which comprise for example, in alternative embodiments not illustrated, acoustic boxes which the user can wear at the ears.

The transducers 15 and 16, together with the respective connecting cables and the audio amplifier 14, form means 17 for communication between the processing system 9 and the user 2 to substantially feed the information about the kinematics of the user's body to the user 2, encoded in a feedback signal defined by the stereophonic sound.

In practice, the definition of the feedback signal is such that it provides the user 2 with the above-mentioned kinematic information relative, for example, to substantially horizontal movements of the torso.

Generally speaking, the accelerations of the body are separated into anteroposterior AP, corresponding to forward A and backward P movements of the torso (or other body segment considered), and mediolateral ML, corresponding to torso movements to the right R or to the left L, and the stereophonic sound is encoded, modulated and balanced between the earphones 12 and 13 on the basis of these.

The sound dynamics inform the user 2 about his/her movement and, in particular, inform the user about movements of which he/she may not otherwise be aware, so that the user can correct his/her position.

FIGS. 3a and 3b illustrate, by way of example, a preferred trend of the volume V and frequency F of the stereophonic sound depending on AP accelerations, whilst FIG. 3c illustrates a preferred trend of the volume V for ML accelerations to the right R and to the left L by the user 2.

Again by way of example, FIG. 3d illustrates balancing B of the stereophonic sound between the right and left earphones 12 and 13 according to ML accelerations by the user 2.

The maximum volume is generated by the maximum torso accelerations, whether they are AP or ML.

Figure 2:
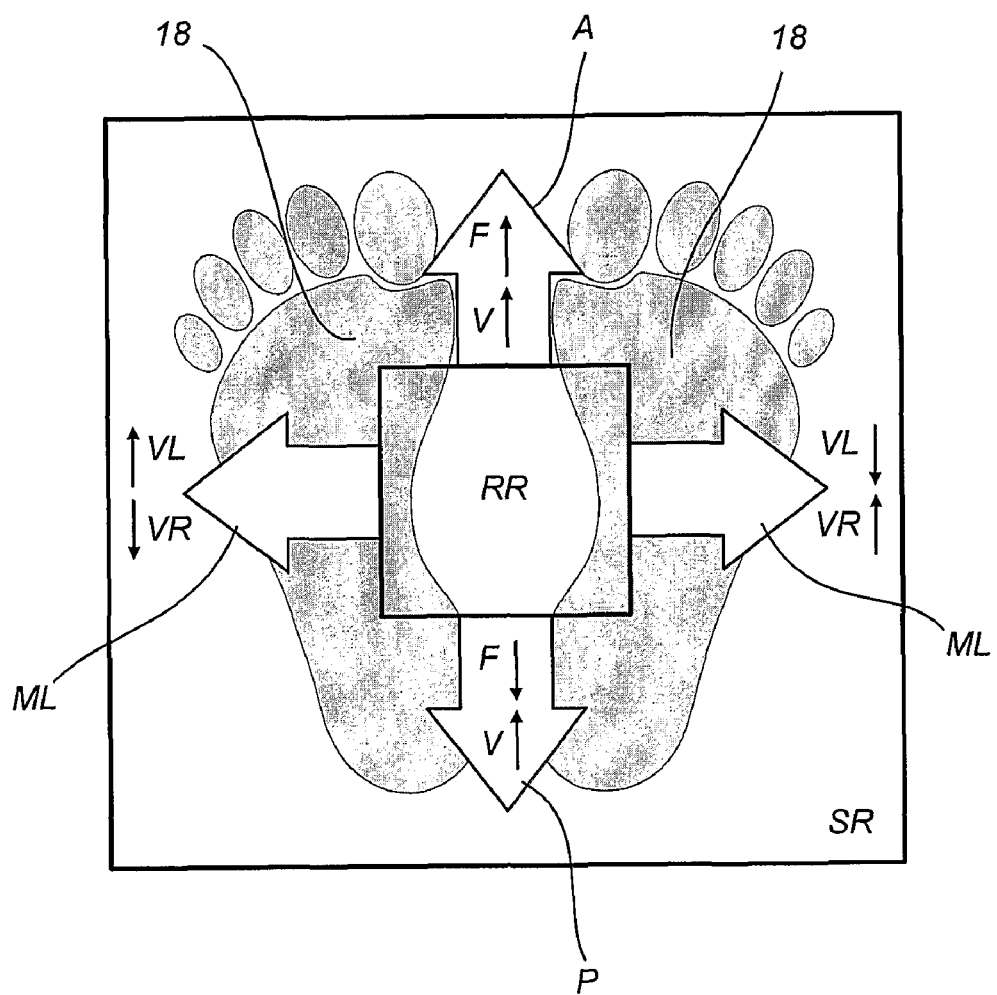
FIG. 2 is a schematic illustration of a method for management of the parameters of the control signal in the device illustrated in FIG. 1.

As schematically illustrated in FIG. 2, in the case of forward movements the frequency F of the sound increases, whilst in the case of backward oscillations the frequency F of the sound is reduced.

It should be observed that an acceleration by the user 2 to the right R causes an increase in the volume in the right VR earphone 12, whilst an acceleration to the left L causes an increase in the volume in the left VL earphone 13. In this way, the user 2 can recognise lateral accelerations by listening to the balance of the sound between the two earphones 12 and 13, right and left.

With reference to FIGS. 3a to 3d, to prevent excessive information feedback to the user 2, the device 1 may advantageously be programmed to consider the existence of a reference region RR, with amplitude between a value $RR_0$ and a value $RR_1$, about the natural posture of the body of the user 2, in which small swaying movements in the torso are completely normal even in perfectly healthy people.

Indeed, maintenance of the erect position is normally the result of a combination of accelerations according to a plurality of angles and directions.

The region RR is used as a reference for generation of the feedback signal and is expressed in terms of AP and ML accelerations.

The amplitude of the region RR depends, for example, on the anthropometry of the user 2 and may be defined according to his/her height with a substantially known inverted pendulum model.

With reference to FIG. 2, it may be seen that a safety region SR is also defined, its amplitude between a value $SR_0$ and a value $SR_1$, depending, in accordance with substantially known methods, on the dimensions of the feet 18 of the user 2.

The limits of the safety region SR represent the maximum travel of the body of the user 2 before the projection of his/her centre of mass leaves a support base formed by the feet 18.

In the region RR the processing system 9 generates a sound, for example, with a frequency value F equal to $f_0 = 400$ Hz and a predetermined volume value V in both earphones 12 and 13.

By way of example, a set of equations designed to define the frequency F and volume V of the feedback signal are shown below.

With reference to FIGS. 3a and 3c, the volume V of the sound may be planned and regulated with a sigmoid law of this type:

$$\text{Volume} = \frac{V1 \times A_i^k}{A_i^k + m^k} + c$$

where $A_i$ is the acceleration measured along two axes (i=AP, ML), k=3 for a forward A oscillation, k=2.5 for a backward P or mediolateral oscillation, m=3, V1=0.5 and c is a constant offset which fixes the minimum volume V of the sound.

With reference to FIG. 3b, the frequency F of the sound for anteroposterior AP accelerations may be planned and regulated, for example between 150 Hz and 1000 Hz, with a linear sectional law of this type:

$$f = \begin{cases} 250 \frac{A_{AP} - SR_0}{RR_0 - SR_0} + 150 & \text{for } A_{AP} \in [SR_0, RR_0] \\ f_0 & \text{for } A_{AP} \in RR \\ 600 \frac{A_{AP} - RR_1}{SR_1 - RR_1} + 400 & \text{for } A_{AP} \in [RR_1, SR_1] \end{cases}$$

With reference to FIG. 3d, balancing of the sound between the two earphones 12 and 13 may be regulated by increasing the volume relative to the side with the prevailing inclination using an exponential law:

$$w = 1 - e^{-10d}$$

where d is the distance between the limits of the reference region RR and the limits of the safety region SR.

The volume in the right earphone 12 and the volume in the left earphone 13 may, therefore, be regulated with laws of this type:

$$VL = (1+w)V$$

$$VR = (1-w)V$$

In the case of oscillations close to the reference region RR, the value of w is set at 0.

Advantageously, in alternative embodiments which are not described, the volume V, frequency F and balancing of the sound are regulated by functions with a different equation and so a different form.

The invention brings important advantages.

The use of an audio signal as feedback for the device user guarantees its practical and simple use.

Advantageously, the device allows the acquisition of automatisms for keeping one's balance without any direct stimulation of the user's nervous system.

The device 1 can also be used by healthy individuals unaffected by particular pathologies, to prevent any postural errors in a non-invasive manner or to boost control or co-ordination of a part of the body, for example, with reference to a sporting technique.

The invention described is suitable for evident industrial applications and may be subject to modifications and variations without thereby departing from the inventive concept. Moreover, all of the details of the invention may be substituted by technically equivalent elements.

The invention claimed is:

1. A device for conditioning the balance and motor coordination of a user, comprising:
    a system for the acquisition of information relative to the kinematics of at least one part of the body of the user,
    a processing system connected to the acquisition system for encoding the information in a stereophonic sound,
    communication means operating between the processing system and the user to provide the user with the information,
    wherein the processing system includes an electronic card configured for modulating the frequency and volume of the stereophonic sound according to an anteroposterior oscillation of the part of the body and for activating the means of communication,
    wherein the communication means comprises a first and a second sound transducer, and
    wherein the electronic card is configured to balance the stereophonic sound between the first and the second sound transducers on the basis of lateral accelerations of the user in such a way that the user can recognize lateral accelerations by listening to the balance of the sound between the two sound transducers.

2. The device according to claim 1, wherein the acquisition system comprises at least one accelerometric sensor attachable to the part of the body.

3. The device according to claim 2, wherein the accelerometric sensor is of the biaxial type.

4. The device according to claim 2, wherein the accelerometric sensor is of the triaxial type.

5. The device according to claim 1,
    wherein the electronic card is configured to generate stereophonic sound comprising right and left signals representing corresponding right and left sound waves, and
    wherein the electronic card is configured to modulate one of the frequency and volume of the right and left sound waves and to balance the stereophonic sound between corresponding right and left audio channels linked to respective earphones which can be worn by the user, each of which includes one of said first and second sound transducers, wherein the electronic card is configured to modulate the right and left channels independently of one another.

6. The device according to claim 5, wherein the first and the second sound transducers comprise a first and a second earphone.

7. The device according to claim 1, wherein the electronic card is configured to modulate the volume of the stereophonic sound according to a mediolateral oscillation of the part of the body.

8. The device according to claim 1, wherein the device is configured to identify oscillation of the torso of the user.

9. The device according to claim 1, wherein the acquisition system, the processing system and the communication means can be worn by the user.

10. A method for conditioning balance and motor co-ordination of a user, comprising the steps of:
    providing a user with a system for the acquisition of information relative to the kinematics of at least one part of the body of the user, a processing system connected to the acquisition system for encoding the information in a stereophonic sound, communication means operating between the processing system and the user to provide the user with the information wherein the processing system includes an electronic card for modulating the frequency and volume of the stereophonic sound according to an anteroposterior oscillation of the part of the body and for activating the means of communication, wherein the communication means comprises a first and a second sound transducer;
    balancing stereophonic sound between the first and the second sound transducers on the basis of lateral accelerations of the user, thus enabling the user to recognize lateral accelerations by listening to the balance of the sound between the two earphones.

* * * * *